United States Patent [19]

Yu

[11] Patent Number: 5,453,360
[45] Date of Patent: Sep. 26, 1995

[54] OXIDATIVE COUPLING DYE FOR SPECTROPHOTOMETRIC QUANTITIVE ANALYSIS OF ANALYTES

[75] Inventor: Yeung S. Yu, Pleasanton, Calif.

[73] Assignee: Lifescan, Inc., Mountain View, Calif.

[21] Appl. No.: 245,940

[22] Filed: May 19, 1994

Related U.S. Application Data

[63] Continuation-in-part of Ser. No. 829,654, Feb. 3, 1992, abandoned.

[51] Int. Cl.[6] .............................. C12Q 1/28; C12Q 1/26; C12Q 1/58; C12Q 1/44
[52] U.S. Cl. ..................... 435/028; 435/25; 435/4; 435/20; 435/19; 435/11; 435/26; 435/14; 435/10; 435/12; 435/810
[58] Field of Search .................... 435/28, 25, 4, 435/20, 19, 11, 26, 14, 10, 12, 810, 966

[56] References Cited

U.S. PATENT DOCUMENTS

| | | | |
|---|---|---|---|
| 4,089,747 | 5/1978 | Bruschi | 435/28 |
| 4,119,405 | 10/1978 | Lam | 422/56 |
| 4,444,789 | 4/1984 | Cormier | 514/517 |
| 4,935,346 | 6/1990 | Phillips et al. | 435/14 |
| 5,049,487 | 9/1991 | Phillips et al. | 422/56 |
| 5,059,394 | 10/1991 | Phillips et al. | 435/14 |
| 5,215,890 | 6/1993 | Theodoropulos et al. | 435/28 |
| 5,332,662 | 7/1994 | Ullman | 435/28 |

FOREIGN PATENT DOCUMENTS

| | | |
|---|---|---|
| 0075894A1 | 4/1983 | European Pat. Off. |
| 87107582 | 12/1987 | Germany |
| WO90/06372 | 6/1990 | WIPO |

OTHER PUBLICATIONS

Ando et al; "A sensitive spectrophotometric assay for guanase activity;" Chem. Abstract; 98(19); 1983.
Elson et al; "Substitution of a non-hazardous chromogen for benzidine in the measurement of plasma hemoglobin;" Chem Abstract; 89(1), 1978.

*Primary Examiner*—David A. Redding
*Assistant Examiner*—Louise N. Leary

[57] ABSTRACT

A dye couple, comprising 3-methyl-2-benzothiazolinone hydrazone (MBTH) and 8-anilino-1-naphthalenesulfonate (ANS), is used as an indicator in a reaction cascade producing a strong oxidizing agent, such as hydrogen peroxide or other peroxides or perborates. The strong oxidizing agent reacts with the dye couple to produce a blue dye stuff. The MBTH-ANS dye couple exhibits strong and flat spectral absorption at the region of about 600 to 650 nm. This region is free of blood color interference, which enables one to measure glucose and other analytes that react with an oxidase enzyme to produce the strong oxidizing agent, through the use of LED optics, accurately without much optic calibration. Further, the MBTH and ANS are very soluble in aqueous solution, yet become insoluble upon oxidative coupling. The poor solubility minimizes dye fading, thus providing a stable endpoint.

13 Claims, 3 Drawing Sheets

OXIDATIVE COUPLING DYE FOR SPECTROPHOTOMETRIC QUANTITIVE ANALYSIS OF ANALYTES

U.S. APPLICATION DATA

This is a continuation-in-part of U.S. Ser. No. 829,654, filed on Feb. 3, 1993.

TECHNICAL FIELD

The present invention relates to a test device and method for the colorimetric determination of chemical and biochemical components (analytes) in aqueous fluids, such as whole blood, and, more particularly, to a dye couple used in such device and method.

BACKGROUND ART

The quantification of chemical and biochemical components in colored aqueous fluids, in particular, colored biological fluids such as whole blood and urine and biological fluid derivatives such as serum and plasma, is of ever-increasing importance. Important applications exist in medical diagnosis and treatment and in the quantification of exposure to therapeutic drugs, intoxicants, hazardous chemicals, and the like. In some instances, the amounts of materials being determined are either so minuscule — in the range of a microgram or less per deciliter or so difficult to precisely determine that the apparatus employed is complicated and useful only to skilled laboratory personnel. In this case, the results are generally not available for some hours or days after sampling. In other instances, there is often an emphasis on the ability of lay operators to perform the test routinely, quickly, and reproducibly outside a laboratory setting with rapid or immediate information display.

One common medical test is the measurement of blood glucose levels by diabetics. Current teaching counsels diabetic patients to measure their blood glucose level from two to seven times a day, depending on the nature and severity of their particular cases. Based on the observed pattern in the measured glucose levels, the patient and physician together make adjustments in diet, exercise, and insulin intake to better manage the disease. Clearly, this information should be available to the patient immediately.

Many blood glucose test methods and test articles are known in the art; these all suffer from a variety of limitations. A new procedure system for the determination of analytes has been shown to overcome these limitations; this procedure system is disclosed and claimed in U.S. Pat. No. 4,935,346 by R. Phillips et al and is assigned to the same assignee as the present application.

The method disclosed and claimed in this patent involves taking a reflectance reading from one surface of an inert porous matrix impregnated with a reagent that will interact with the analyte to produce a light-absorbing reaction product when the fluid being analyzed is applied to another surface and migrates through the matrix to the surface being read. The reagent includes glucose oxidase, which consumes glucose in the sample to produce hydrogen peroxide, which then reacts with a dye couple comprising 3-methyl-2-benzothiazolinone hydrazone hydrochloride (MBTH) and 3-dimethylaminobenzoic acid (DMAB) to yield a blue color dye stuff. Reflectance measurements are then made at two separate wavelengths. The concentration of the glucose in blood is determined based on the intensity of the dye color with the aid of a LED spectrophotometer.

The method disclosed and claimed in the above-mentioned patent represents an important step forward in the measurement of blood glucose levels. However, in order to avoid spectral interference with hemoglobin, the glucose measurement is set at 635 nm (in the blue spectral region). This wavelength coincides with the sloping portion of the MBTH-DMAB spectrum, making precise photometric determination difficult without an extensive calibration of the light emitting diode (LED) optics.

Further, the MBTH-DMAB dye couple is very soluble in aqueous media. As the dye forms by the oxidative reaction with hydrogen peroxide, it is prone to migrate away from the reaction zone. Consequently, color intensity gradually decreases with time, thus making the precise endpoint determination of the reaction difficult.

Thus, a need remains in the art to provide a dye couple which produces a blue compound, exhibits a substantially flat absorption in the blue spectral region, and is substantially insoluble in aqueous media upon coupling.

DISCLOSURE OF INVENTION

In accordance with the invention, a dye couple, comprising 3-methyl-2-benzothiazolinone hydrazone (MBTH) (free form or acid form) and 8-anilino-1-naphthalenesulfonate (ANS) (acid form or salt form), is used in place of the MBTH-DMAB dye couple of the prior art. The MBTH-ANS dye couple of the invention exhibits strong and flat spectral absorption at the region which is free of blood color interference. This enables one to measure glucose, for example, through the use of LED optics, accurately without much optic calibration. Further, the MBTH and ANS are very soluble in aqueous solution, yet become insoluble upon oxidative coupling. The poor solubility minimizes dye fading, thus providing a stable endpoint.

The dye couple of the invention is useful as an indicator in a reaction cascade having a strong oxidizing agent, which then drives development of the dye couple to produce a blue dye stuff.

Figure 1:
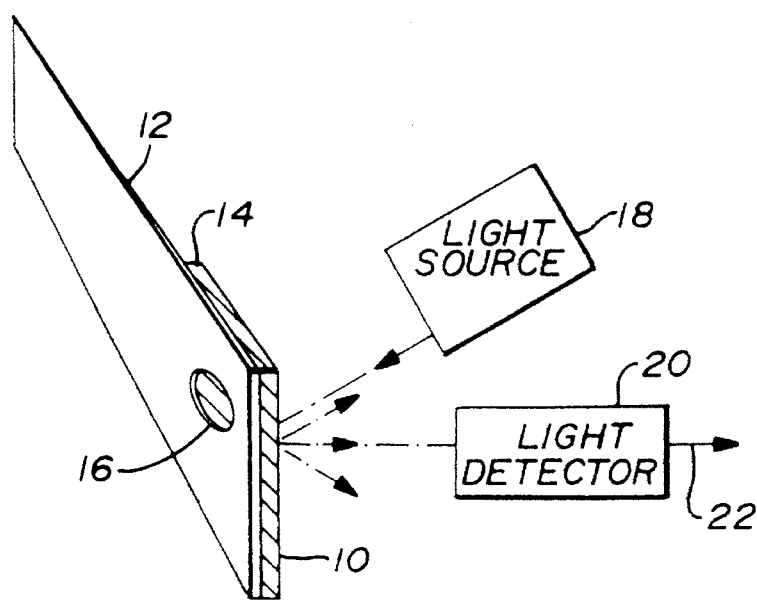
FIG. 1 is a perspective view of one embodiment of a test device containing a reaction pad to which the fluid being analyzed is applied.

BEST MODES FOR CARRYING OUT THE INVENTION 3-methyl-2-benzothiazolinone hydrazone hydrochloride (MBTH) (I) has been found to undergo oxidative coupling with various functionalized aromatic compounds to yield dye stuffs.

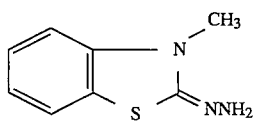

For example, it couples with 3-dimethylaminobenzoic acid (DMAB) (II) and phenol oxidatively to produce a blue and a red compound, respectively.

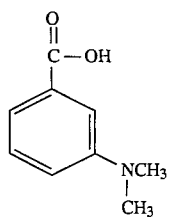

These coupling reactions have been applied in clinical diagnostic techniques.

Owing to the intensity of hemoglobin absorption, dye which has absorption in the red spectrum is avoided, and blue is preferred. This is because at that range, it is free from hemoglobin spectral interference. As noted above, the prior art, represented by U.S. Pat. No. 4,935,346, utilizes the blue MBTH-DMAB dye.

In the present invention, MBTH couples with 8-anilino-1-naphthalenesulfonate (ANS) (III) to afford a blue compound. Here, the ammonium salt is depicted.

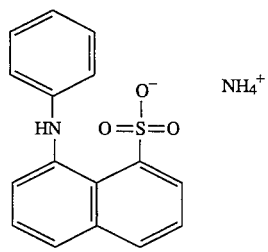

The coupled dye exhibits a strong and flat absorption at the hemoglobin-free zone. Such spectral characteristic has significantly improved the accuracy of the testing results without the extensive LED calibration previously required.

Additionally, the coupled dye becomes insoluble in aqueous media upon coupling, thus minimizing dye fading. With that, it yields a flat endpoint. Such feature would be desirable for the purpose of non timing-dependent analysis. This means that the test does not require precise initial timing on the onset of measurement, and the final measurement, which is important for determining the concentration of the analyte, can be taken within a broader window of time.

The MBTH dye may be present in the free form or in the acid form. Examples of the latter include the hydrochloride and sulfate forms. The term 3-methyl-2-benzothiazolinone hydrazone is intended to cover all forms in which the dye may be employed in the practice of the invention.

The ANS dye may be present in the acid form (as sulfonic acid) or in the salt form. Examples of cations suitably employed in the latter include magnesium, ammonium, sodium, and potassium. The term 8-anilino-1-naphthalenesulfonate is intended to cover all forms in which the dye may be employed in the practice of the invention.

A. The Reagent Element

The present invention provides an improved rapid and simple methodology employing reliable and easy to operate apparatus for the determination of analytes such as glucose, particularly involving an enzyme substrate which results in the production of hydrogen peroxide or other strong oxidizing agents as an enzyme product. That is, the dye couple of the invention may be employed as an indicator in a reaction cascade resulting in a strong oxidizing agent, which reacts with the dye couple to form a blue dye stuff.

Examples of enzyme products which drive the development of the dye couple include hydrogen peroxide ($H_2O_2$), such as generated from the interaction of glucose with glucose oxidase enzyme or from other enzyme reactions, and other peroxides, such as cumene hydrogen peroxide, urea hydrogen peroxide, benzoyl peroxide, and perborates, such as the sodium, potassium, or other salt form or the acid form thereof.

The method involves applying to a porous matrix a small volume of whole blood, sufficient to saturate the matrix. Bound to the matrix are one or more reagents of a signal-producing system, which results in the production of a product resulting in an initial change in the amount of reflectance of the matrix. The matrix is typically present in a reflectance-measuring apparatus when blood is applied. The liquid sample penetrates the matrix, resulting in an initial change in reflectance at the measurement surface. A reading is then taken at one or more times after the initial change in reflectance to relate the further change in reflectance at the measurement surface or in the matrix as a result of formation of the reaction product to the amount of analyte in the sample, For measurements in blood, such as glucose measurements, whole blood is typically used as the assay medium. The matrix contains an oxidase enzyme which produces hydrogen peroxide. Also contained in the matrix is a second enzyme, particularly a peroxidase, and a dye system which produces a light-absorbing product in conjunction with the peroxidase. The light-absorbing product changes the reflectance signal. With whole blood, readings are taken at two different wavelengths, with the reading at one wavelength used to subtract out background interference cause by hematocrit, blood oxygenation, and other variables which may affect the result.

A pseudo-peroxidase may alternately be employed; examples include hemoglobin, which acts catalytically like an enzyme, and other metallo-organic compounds which exhibit peroxidase-like activity, such as tetrakis [sulphophenyl]porphyrin manganese.

The details of the reagent element and its use are set forth with more particularity in U.S. Pat. No. 4,935,346, and need not be described further herein. Essentially, the reagent element is in the shape of a pad, comprising an inert porous matrix and the component or components of a signal-producing system, which system is capable of reacting with an analyte to produce a light-absorbing reaction product, impregnated into the pores of the porous matrix.

In use, briefly, the liquid sample being analyzed is applied to one side of the sheet whereby any assay compound passes through the reagent element by means of capillary, wicking, gravity flow, and/or diffusion actions. The components of the signal producing system present in the matrix will react to give a light absorbing reaction product. Incident light impinges upon the reagent element at a location other than the location to which the sample is applied. Light is reflected from the surface of the element as diffuse reflected light. This diffuse light is collected and measured, for example by the detector of a reflectance spectrophotometer. The amount of reflected light will be related to the amount of analyte in the sample, usually being an inverse function of the amount of analyte in the sample.

B. The Matrix

The matrix and its preparation are also set forth in detail in the above-referenced U.S. Pat. No. 4,935,346 and need not be described in detail herein. Essentially, the matrix is a hydrophilic porous matrix to which reagents may be covalently or non-covalently bound. Examples of a suitable matrix material include polyamides, which are conveniently condensation polymers of monomers of from 4 to 8 carbon atoms, where the monomers are lactams or combinations of diamines and di-carboxylic acids, polysulfones, polyesters, polyethylene, and cellulose-base membranes. Other polymeric compositions may also be used. Further, the polymer compositions may be modified to introduce other functional groups so as to provide for charged structures, so that the surfaces may be neutral, positive, or negative, as well as neutral, basic, or acidic.

Typically, the matrix is attached to a holder in order to give it physical form and rigidity, although this may not be necessary. FIG. 1 shows one embodiment wherein a thin hydrophilic matrix pad 10 is positioned at one end of a plastic holder 12 by means of an adhesive 14 which directly and firmly attaches the reagent pad to the handle. A hole 16 is present in the plastic holder 12 in the area to which the reagent pad 10 is attached so that sample can be applied to one side of the reagent pad and light reflected from the other side.

A liquid sample to be tested is applied to pad 10. As can be seen from FIG. 1, the support holds the reagent pad 10 so that a sample can be applied to one side of the pad while light reflectance is measured from the side of the pad opposite the location where sample is applied, through opening 16.

Light is directed onto the pad 10 from light source 18. Any reflected light is measured by a detector 20 and the resulting signal 22 is processed by subsequent means (not shown).

Figure 1A:
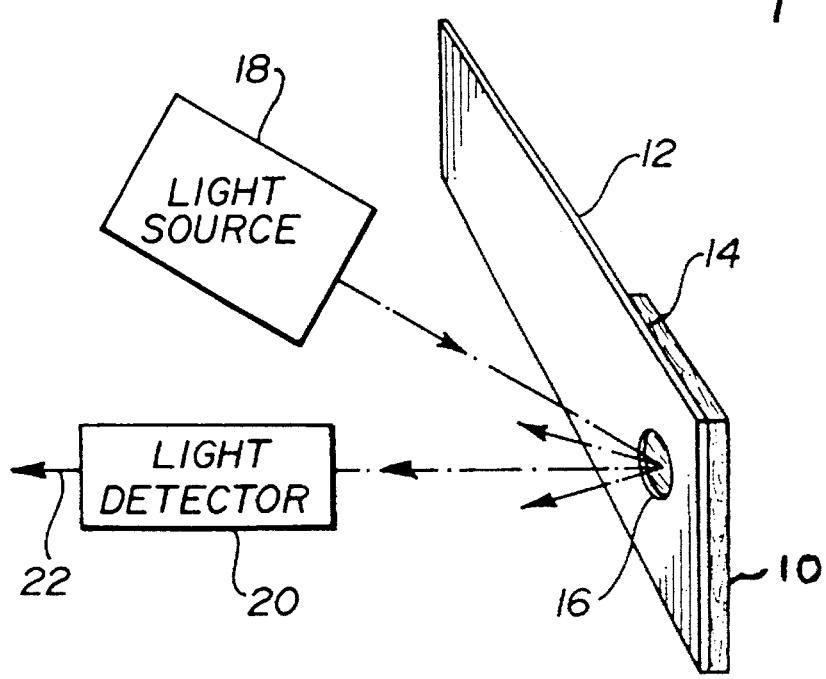
FIG. 1A is a perspective view of a second embodiment of the employment of the test device of FIG. 1.

In FIG. 1A a second embodiment of the employment of the device of FIG. 1 is illustrated. In this case, the sample is applied to the surface of matrix pad 10 that is unattached to the plastic holder 12 and light is directed at the opposite surface of the matrix pad 10 through the aperture 16, with light detector 20 measuring the reflectance from this surface.

C. The Chemical Reagents

The chemical reagents, except for the specific dye-couple which is the subject of the present invention, are also set forth in the above-referenced U.S. Pat. No. 4,935,346. In one embodiment, an analyte reacts with an oxygen-utilizing oxidase enzyme in such a manner that a product is produced that further reacts with a dye intermediate to either directly or indirectly form a dye which absorbs in a predetermined wavelength range. For example, an oxidase enzyme, such as glucose oxidase, oxidizes an analyte, such as glucose, and produces hydrogen peroxide as a reaction product. The hydrogen peroxide then reacts with the dye couple MBTH/ANS to produce the blue colored dye stuff.

Other examples include (a) the determination of cholesterol, using cholesterol oxidase, (b) the determination of uric acid, using uricase, (c) the determination of methanol and ethanol, using alcohol oxidase, (d) the determination of formaldehyde, using aldehyde oxidase, and (e) the determination of glycerol-3-phosphate, using glycerophosphate oxidase. In all cases, hydrogen peroxide is produced as the reaction product, which then reacts with the dye couple.

D. The Analysis Method

The analysis method of this invention relies on a change in absorbance, as measured by diffuse reflectance, which is dependent upon the amount of analyte present in a sample being tested. This change may be determined by measuring the change in the absorbance of the test sample between two or more points in time.

The first step of the assay to be considered is the application of the sample to the matrix. In practice, an analysis could be carried out as follows: First, a sample of aqueous fluid containing an analyte is obtained. Blood may be obtained by a finger stick., for example. An excess over matrix saturation in the area where reflectance will be measured (e.g., about 5 to 10 microliters) of this fluid is applied to the reagent element or elements of the test device. Simultaneous starting of a timer is not required. Excess fluid may be removed, such as by light blotting, but is also not required. The test device is typically mounted in an instrument for reading light absorbance, e.g., color intensity, by reflectance, prior to application of the sample. Absorbance is then measured at certain points in time after application of the sample. From these measurements of absorbance, a rate of color development can be calibrated in terms of analyte level.

E. The Measuring Instrument

A suitable instrument employed in the practice of the invention is a diffuse reflectance spectrophotometer with appropriate software, such as described in the above-referenced U.S. Pat. No. 4,935,346. Such an instrument can be made to automatically read reflectance at certain points in time, calculate rate of reflectance change, and, using calibration factors, output the level of analyte in the fluid.

F. Particular Applications to Glucose Assay

A particular example with regard to detecting glucose in the presence of red blood cells will now be given in order that greater details and particular advantages can be pointed out. Although this represents a preferred embodiment of the present invention, the invention is not limited to the detection of glucose in blood. In this connection, the matrix used in the analysis may be formed from any water-insoluble hydrophilic material and any other type of reflectance assay, as described above.

The dye couple employed herein, MBTH/ANS, is preferably present in a molar ratio of about 3:7. However, due to stability considerations, a slight excess of MBTH, up to about 20 molar percent, may be present.

A typical formulation for the glucose reagent is as follows:

Aqueous Dip

Combine:

20 ml water;

420 mg citric acid (a buffering agent);

Adjust the pH of the citric acid solution with NaOH (e.g., 50% aqueous solution) to a value of about 4.0 to 4.5, and preferably about 4.25;

16.7 mg ethylene diamine tetraacetic acid (a sequestering agent to remove unwanted heavy metals);

90 mg GANTREZ S95 (a color fixing agent, comprising a polyvinyl acid, available from GAF (New York, N.Y.);

250 mg CROTEIN SPA (a protein stabilizer, comprising hydrolyzed collagens, available from Croda (New York, N.Y.);

20,500 units glucose oxidase; and 16,200 units peroxidase.

Organic Dip

Combine:

10 ml of a mixture of 3 parts by volume water and 7 parts by volume iso-propyl alcohol;

5 to 30 mg MBTH, preferably 11 mg; and 5 to 60 mg ANS, preferably 38 mg.

A strip of the membrane (matrix) material is cut to the desired shape and size and is dipped into the aqueous solution to saturate the membrane. The strip is removed from the aqueous dip and any excess liquid is squeegeed off. The strip is then hung vertically in an air circulating oven at 56° C. ±5° C. for about 5 to 10 minutes to dry. The dried strip is then dipped into the organic solution to again saturate the membrane. The strip is removed from the organic dip and any excess liquid is squeegeed off. The strip is again dried as above. The dried strip is now ready to be applied to the applicator and may be used in the detection of an analyte.

Figure 2:
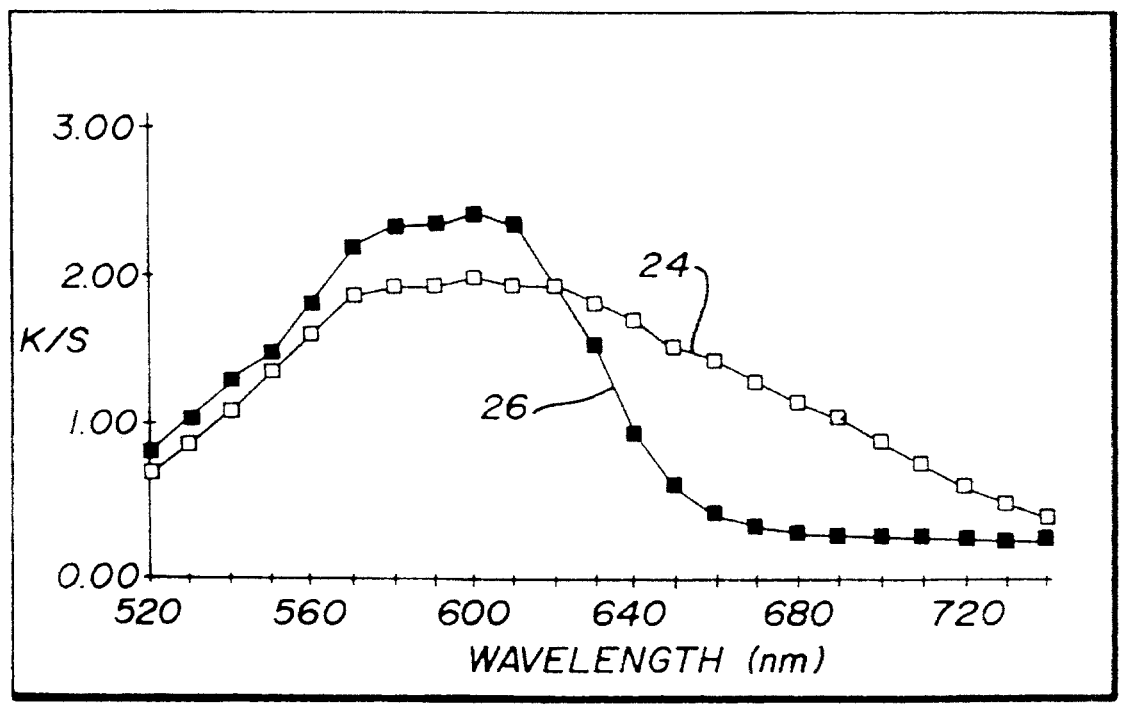
FIG. 2, on coordinates of reflectance (K/S units) and wavelength (in nm), is a plot comparing the spectra of MBTH-ANS and MBTH-DMAB over the wavelength region of 520 to nm.
Figure 3:
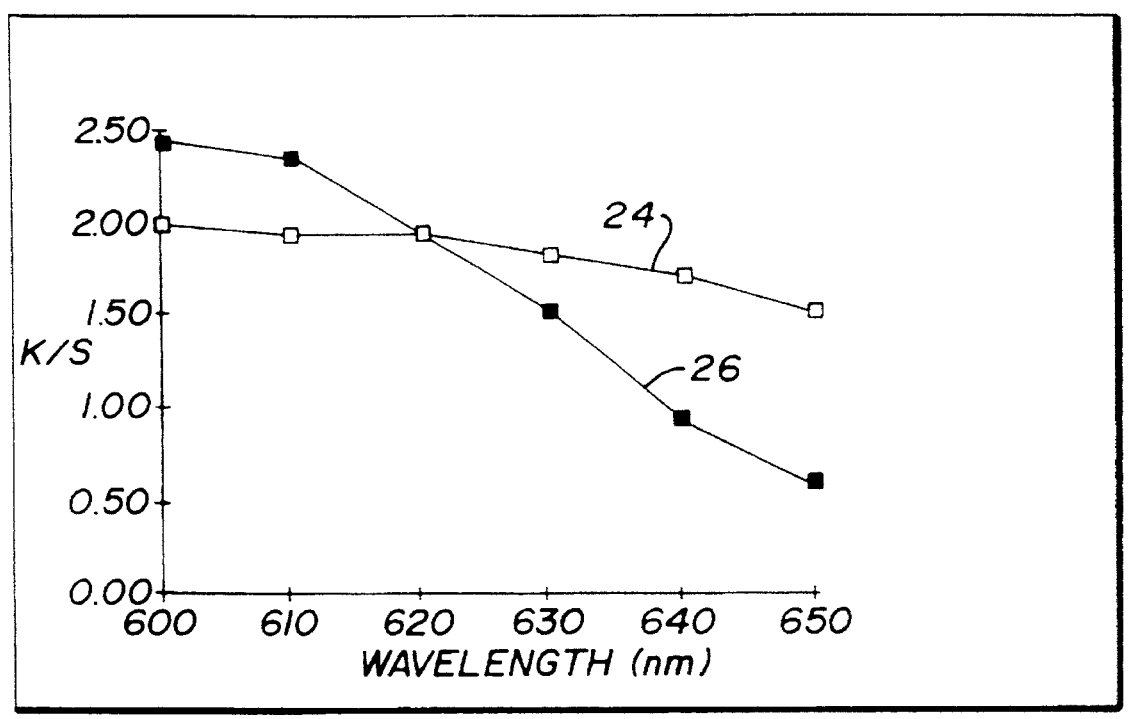
FIG. 3 is a plot similar to that of FIG. 2, except over a limited wavelength region of 600 to 650 nm.

The reflectance spectra of MBTH-ANS (dye couple of the invention) and MBTH-DMAB (dye couple of the prior art) were taken and are shown in FIGS. 2 and 3. Curve 24 represents MBTH-ANS, while Curve 26 represents MBTH-DMAB. As is seen in FIG. 2, a desirably broader band at the maximum wavelength is obtained for the dye couple of the invention. As seen in FIG. 3, there is a substantially flat region in the reflectance spectrum between 600 and 650 nm for the dye couple of the invention. The significance of this is that an error in the wavelength at which measurement is made, which is nominally 635 nm, has little effect on the spectral response.

Test strips were prepared using the above dips, and glucose solutions of various concentrations were measured by placing an amount of the solution on a test strip and measuring the reflectance at 635 nm, using a reflectance spectrophotometer such as described in U.S. Pat. No. 4,935,346. The measured reflectance as a function of glucose concentration is listed in Table I below.

TABLE I

Reflectance as a Function of Glucose Concentration.

| Glucose Concentration | Δ Reflectance |
|---|---|
| 0 mg/dl | 0 |
| 100 mg/dl | 100Δ |
| 200 mg/dl | 200Δ |
| 300 mg/dl | 300Δ |
| 400 mg/dl | 400Δ |

The reflectance is in arbitrary units, as indicated by the multiplier Δ. It is seen that the reflectance using the dye couple of the invention is linear with glucose concentration.

In actual use, a drop of blood is placed on one side of the matrix pad 10. The plastic holder 12 is inserted in the optical path of the instrument, and the resulting reflectance is measured at 635 nm. This value is compared to a calibration table stored, for example, in the microprocessor of the measuring instrument. A value corresponding to the glucose level is then output for use by the operator.

INDUSTRIAL APPLICABILITY

The dye couple of the invention is useful in a variety of reactions in which a strong oxidizing agent is created to indicate the presence and/or concentration of an analyte.

Thus, there has been disclosed a dye couple for use as an indicator in a reaction cascade producing a strong oxidizing agent. It will be apparent to one of ordinary skill in the art that various changes and modifications of an obvious nature may be made without departing from the spirit or scope of the invention, as defined by the following claims.

What is claimed is:

1. A test device containing a reaction pad to which a fluid to be analyzed is to be applied, said reaction pad including a hydrophilic matrix pad supported on a substrate holder, said reaction pad having pores containing a reagent system comprising an oxidase enzyme, a peroxidase, and a dye indicator comprising 3-methyl-2-benzothiazolinone hydrazone and 8-anilino-1-naphthalene sulfonate.

2. The test device of claim 1 wherein said oxidase enzyme is selected from the group consisting of glucose oxidase, cholesterol oxidase, uricase, alcohol oxidase, aldehyde oxidase, and glycerophosphate oxidase.

3. A test device containing a reaction pad to which an aqueous fluid to be analyzed is to be applied, said reaction pad including a hydrophilic matrix pad supported on a substrate holder, said reaction pad having pores containing a reagent system comprising an oxidase enzyme, a peroxidase, and a dye indicator, said dye indicator comprising 3-methyl-2-benzothiazolinone hydrazone and 8-anilino-1-napthalene sulfonate.

4. The test device of claim 3 wherein said oxidase enzyme is selected from the group consisting of glucose oxidase, cholesterol oxidase, uricase, alcohol oxidase, aldehyde oxidase, and glycerophosphate oxidase.

5. A method of determining analyte concentration in a liquid which comprises:

(a) quantitatively measuring baseline reflectance from a first surface of a reagent element comprising an inert, porous, hydrophilic, substantially reflective, single-layer matrix having pores of a size sufficient to exclude red blood cells and a reagent system which interact with said analyte to produce a light-absorbing reaction product, said reagent system being impregnated in the pores of said matrix, prior to application of said liquid to said reagent element;

(b) applying said liquid to a second surface of said reagent element and allowing said liquid to migrate from said second surface to said first surface;

(c) quantitatively measuring reaction reflectance from said first surface of said reagent element without removing excess sample or non-migrating components of said sample from said second surface;

(d) quantitatively measuring reflectance of interfering substances from said first surface of said reagent element using a wavelength of light reflected by interfering substances and different from the wavelength of light used to measure said reaction product reflectance in order to correct for background reflectance at the reaction product wavelength caused by interfering substances; and (e) calculating a value expressing said analyte concentration from said reflectance measurements, wherein said reaction system includes a dye couple consisting essentially of 3-methyl-2-benzothiazolinone hydrazone and 8-anilino-l-naphthalene sulfonate and at least one reagent capable of reacting with said analyte to produce a strong oxidizing agent which reacts with said dye couple to form a blue dye.

6. The method of claim 5 wherein said strong oxidizing agent is selected from the group consisting of hydrogen peroxide and peroxides.

7. The method of claim 6 wherein said organic peroxides are selected from the group consisting of cumene hydrogen peroxide, urea hydrogen peroxide, benzoyl peroxide, and perborates.

8. The method of claim 6 wherein said analyte comprises glucose and said reaction system further includes glucose oxidase and peroxidase.

9. A method of determining analyte concentration in a liquid which comprises:

(a) quantitatively measuring baseline reflectance from a first surface of a reagent element comprising an inert, porous, hydrophilic, substantially reflective, single-layer matrix having pores of a size sufficient to exclude red blood cells and a reagent system which interact with said analyte to produce a light-absorbing reaction product, said reagent system being impregnated in the pores of said matrix, prior to application of said liquid to said reagent element;

(b) applying said liquid to a second surface of said reagent element and allowing said liquid to migrate from said second surface to said first surface;

(c) quantitatively measuring reaction reflectance from said first surface of said reagent element without removing excess sample or non-migrating components of said sample from said second surface;

(d) quantitatively measuring reflectance of interfering substances from said first surface of said reagent element using a wavelength of light reflected by interfering substances and different from the wavelength of light used to measure said reaction product reflectance in order to correct for background reflectance at the reaction product wavelength caused by interfering substances; and (e) calculating a value expressing said analyte concentration from said reflectance measurements, wherein said analyte comprises a substance that reacts with an enzyme to produce hydrogen peroxide and said reagent system comprises said enzyme, peroxidase and 3-methyl-2-benzothiazolinone hydrazone and 8-anilino-1-naphthalene sulfonate.

10. The method of claim 9 wherein said analyte comprises a substance selected from the group consisting of glucose, cholesterol, uric acid, methanol, ethanol, formaldehyde, and glycerol-3-phosphate.

11. The method of claim 9 wherein said enzyme is selected from the group consisting of glucose oxidase, cholesterol oxidase, uricase, alcohol oxidase, aldehyde oxidase, and glycerophosphate oxidase.

12. In a method for determining glucose in a blood sample employing a membrane and a signal-producing system which reacts with glucose to produce a light-absorptive dye product, said system being bound to the membrane, and in which the amount of said dye product is determined by means of a reflectance measurement from a surface of said membrane, said method comprising:

(a) applying an unmeasured whole blood sample to a first surface of a single-layer, substantially reflective, porous, hydrophilic membrane having pores of a size sufficient to exclude red blood cells and which contains said signal-producing system;

(b) making said reflectance measurement on a second surface of said membrane other than the surface to which said sample is applied without removing excess sample or red blood cells from said first surface; and (c) determining the concentration of glucose in said sample from said reflectance measurement, wherein the improvement comprises employing as said signal-producing system glucose oxidase, peroxidase and 3-methyl- 2-benzothiazolinone hydrazone and 8-anilino-1-naphthalene sul-fonate.

13. A method for determining glucose comprising the steps of:

(a) applying a whole blood sample to an application site on a reagent element wherein said reagent element comprises a single-layer, substantially reflective, porous, hydrophilic matrix which filters out red blood cells and to which is bound a signal-producing system comprising glucose oxidase, peroxidase, and a dye indicator, which signal-producing system reacts with glucose to form a reaction dye product;

(b) allowing the sample to migrate to a reading site on said membrane different from said application site;

(c) monitoring reflectance at said reading site for a decrease in reflectance indicative of sample presence in said reading site in order to initiate timing of an incubation period; and (d) determining the change in reflectance at said reading site during the incubation period as a measure of dye product formed to determine the amount of glucose in said sample, in which all reflectance measurements at said reading site are performed without removing excess sample or red blood cells from said application site and at least one measurement is taken at a wavelength at which light is absorbed by said dye product, wherein said dye indicator comprises 3-methyl-2-benzothiazolinone hydrazone and 8-anilino-1-naphthalene sulfonate.

* * * * *

UNITED STATES PATENT AND TRADEMARK OFFICE
CERTIFICATE OF CORRECTION

PATENT NO. : 5,453,360
DATED : September 26, 1995
INVENTOR(S) : Yeung S. Yu

It is certified that error appears in the above-indentified patent and that said Letters Patent is hereby corrected as shown below:

Title page, item [54] and column 1, lines 2 and 3, the title should read "Oxidative Coupling Dye for Spectrophotometric Quantitative Analysis of Analytes"

Signed and Sealed this

Sixteenth Day of April, 1996

BRUCE LEHMAN

Attest:

Attesting Officer

Commissioner of Patents and Trademarks